US012766086B2

(12) United States Patent
Cheng

(10) Patent No.: US 12,766,086 B2
(45) Date of Patent: Oct. 20, 2026

(54) DIETARY SUPPLEMENT FOR IMPROVING SKIN APPEARANCE

(71) Applicant: Pique Life Pte. Ptd., Singapore (SG)

(72) Inventor: Simon Cheng, Beverly Hills, CA (US)

(73) Assignee: Pique Life Pte. Ltd., Singapore (SG)

( * ) Notice: Subject to any disclaimer, the term of this patent is extended or adjusted under 35 U.S.C. 154(b) by 558 days.

(21) Appl. No.: 18/302,711

(22) Filed: Apr. 18, 2023

(65) Prior Publication Data

US 2023/0330000 A1 Oct. 19, 2023

Related U.S. Application Data

(60) Provisional application No. 63/332,221, filed on Apr. 18, 2022.

(51) Int. Cl.

| | |
|---|---|
| ***A61K 8/73*** | (2006.01) |
| ***A61K 8/19*** | (2006.01) |
| ***A61K 8/42*** | (2006.01) |
| ***A61K 8/96*** | (2006.01) |
| ***A61K 8/9794*** | (2017.01) |
| ***A61Q 19/00*** | (2006.01) |

(52) U.S. Cl.

CPC ................ *A61K 8/735* (2013.01); *A61K 8/19* (2013.01); *A61K 8/42* (2013.01); *A61K 8/965* (2013.01); *A61K 8/9794* (2017.08); *A61Q 19/00* (2013.01); *A61K 2800/92* (2013.01)

(58) Field of Classification Search

None

See application file for complete search history.

(56) References Cited

FOREIGN PATENT DOCUMENTS

WO WO-2021014153 A1 * 1/2021 ............... A61K 8/11

OTHER PUBLICATIONS

Sodium Hyaluronate vs. Hyaluronic Acid: What's the Difference?. Retrieved on: Mar. 28, 2025, available on: Nov. 28, 2020. Retrieved from the internet < https://pharmagel.net/pages/sodium-hyaluronate-vs-hyaluronic-acid-what-s-the-difference> (Year: 2020).*

Can Electrolytes Help Keep Your Skin Hydrated?. Sobel retrieved on: Mar. 28, 2025 and available on: Jun. 7, 2021. Retrieved from the internet <https://nakednutrition.com/blogs/supplements/electrolytes-hydration-skin-health?srsltid=AfmBOorU0DeVolrqJkMU-wdxogcVhi6sBD9mAjngZJZczRI0iAvw_NDH> (Year: 2021).*

Hakimian, J., Goldbarg, S. H., Park, C. H., & Kerwin, T. C. (2014). Death by coconut. Circulation: Arrhythmia and Electrophysiology, 7(1), 180-181. (Year: 2014).*

Does pink Himalayan salt have any health benefits?. Leonard retrieved on: Mar. 28, 2025, available on: Jul. 30, 2018. Retrieved from the internet < https://www.medicalnewstoday.com/articles/315081> (Year: 2018).*

Potassium. Retrieved on: Mar. 28, 2025 available on: Mar. 22, 2021. Retrieved from the internet <https://ods.od.nih.gov/factsheets/Potassium-Consumer/#:~:text=Potassium%20in%20supplements%20comes%20in,is%20better%20than%20the%20others.> (Year: 2021).*

Everything you should know about magnesium glycinate. Retrieved on: Mar. 31, 2025 Available on Sep. 20, 2019. Retrieved from the internet < https://consensus.app/home/blog/everything-you-should-know-about-magnesium-glycinate/> (Year: 2019).*

Reinwald, S., Weaver, C. M., & Kester, J. J. (2008). The health benefits of calcium citrate malate: a review of the supporting science. Advances in food and nutrition research, 54, 219-346. (Year: 2008).*

Salt vs. Sodium Citrate. Retrieved on Mar. 31, 2025 Available on: Sep. 21, 2020. Retrieved from the internet < https://nuunlife.com/blogs/news/salt-vs-sodium-citrate>. (Year: 2020).*

Nuun Vitamins. Retrieved on: Apr. 1, 2025 available on: Aug. 29, 2020. Retrieved from the internet <https://nuunlife.com/products/nuun-vitamins> (Year: 2020).*

Bizot et al., "Improving Skin Hydration and Age-related Symptoms by Oral Administration of Wheat Glucosylceramides and Digalactosyl Diglycerides: A Human Clinical Study," Cosmetics, vol. 4, No. 37, p. 1-17 (Sep. 21, 2017).

Seppic, "Ceramosides™," p. 1-4 (Apr. 1, 2020).

Seppic, "Address key signs of skin aging with clinically-studied Ceramnosides™," p. 1-12 (Mar. 14, 2018).

* cited by examiner

*Primary Examiner* — Melissa L Fisher

(74) *Attorney, Agent, or Firm* — Dergosits & Noah LLP

(57) ABSTRACT

Provided is a dietary supplement and method of use that promote skin hydration and thus improve its appearance. The supplement includes a form of hyaluronic acid and at least one ceramide—the hyaluronic acid promoting water retention in the deep layers of the epidermis and the ceramide promoting the surface retention of moisture.

12 Claims, No Drawings

DIETARY SUPPLEMENT FOR IMPROVING SKIN APPEARANCE

CROSS-REFERENCE TO RELATED CASES

The application claims priority to U.S. Provisional Patent Application No. 63/332,221, entitled "Dietary Supplement For Improving Skin Appearance," filed Apr. 18, 2022, which is hereby incorporated by reference.

BACKGROUND

As people age, the skin's lipid barrier breaks down due to a natural reduction in ceramide production. The dehydrative effects of this loss in barrier integrity are compounded by the natural decline in the production of hyaluronic acid (which attracts and binds to water to replenish moisture in skin). UV rays, environmental toxins, and aging can also reduce the amount of hyaluronic acid in the body. The skin then develops wrinkles, fine lines, and dryness. This accounts for younger people having smoother, plumper looking skin, in comparison to those with more years in life.

Thus, what is needed is a dietary supplement for improving skin appearance.

BRIEF SUMMARY

In an embodiment, a dietary supplement for improving skin appearance includes at least one ceramide, and hyaluronic acid.

In an embodiment, a dietary supplement for improving skin appearance includes an electrolyte replenishment, in liquid or powder forms, which also includes ceramides and hyaluronic acid.

In an embodiment, a combination of electrolytes and ceramides and hyaluronic acid is designed to provide total cellular and epidermal hydration from the inside out (through supplementation).

Embodiments may include both powder and liquid versions. Benefits of such embodiments include one or more of: improved skin elasticity; reduced fine skin lines; reduced skin wrinkles; reduced skin dryness; reduced skin flakiness; a youthful, dewy skin glow; deep cellular hydration; deep skin hydration; healthy-aging skin; youthful-appearing skin; plump, firm, and dewy skin; a regulating of fluid balance, inside and out; and a clearing of brain fog.

DETAILED DESCRIPTION

Embodiments include a breakthrough in skin hydration in the form of a dietary supplement, which includes a form of hyaluronic acid and at least one ceramide, and which enhances cellular absorption of bioactive compounds for a truly transformative and youth-enhancing skin supplement. In such embodiments, hyaluronic acid promotes water retention in the deep layers of the epidermis and ceramides promote the surface retention of skin moisture. In embodiments, the dietary formula uses synergistic properties of natural compounds to hydrate the skin and improve its appearance.

Ceramides are included in embodiments because they are clinically proven to strengthen skin hydration and improve elasticity while visibly reducing fine lines and dullness. Ceramide replenishment restores skin barrier function and strengthens cellular integrity to reduce moisture loss. Ceramides may be obtained from phytoceramides. Hyaluronic Acid is included in embodiments because its replenishment in the skin helps the skin soak up and retain moisture, which is a foundation for a youthful, dewy glow. Hyaluronic Acid may be obtained from premium sodium hyaluronate with an ultra-low molecular weight and maximized for cellular absorption.

In some embodiments, the dietary supplement includes minerals, which deliver deep cellular hydration via bioavailable forms of mineral chelates combined with trace minerals from Himalayan pink salt and pure coconut water. In embodiments, the mineral stack (Ca, Mg, Na, and K, as found in the dietary supplement compositions below) is designed to enhance rapid absorption of electrolytes and bioactive compounds into your cells. The mineral stack hydrates on a cellular level while providing a transport system for rapid and maximized absorption.

In an embodiment of a dietary supplement, the composition is:

Serving Size: 1 sachet (3.75 g); Servings Per Container: 28

Ingredient; Amount Per Serving; % RDV (recommended daily value)

Calcium (as Calcium Malate); 30 mg; 3%

Magnesium (as Magnesium Glycinate); 100 mg; 24%

Sodium (as Sodium Citrate and/or Sodium Chloride); 150 mg; 7%

Potassium (as Potassium Citrate and/or Potassium Chloride); 150 mg; 3%

Phytoceramides; 30 mg; **

Sodium Hyaluronate; 30 mg; **

**Daily Value (% RDV) not established.

In an embodiment of a dietary supplement, the composition is:

Serving Size: 1 sachet (3.75 g); Servings Per Container: 28

Ingredient; Amount Per Serving:

Calcium Malate; 30 mg (7 mg calcium)

Magnesium Glycinate; 100 mg (14 mg magnesium)

Either: Sodium Citrate and/or Sodium Chloride; 150 mg (40 mg or 59 mg sodium, respectively)

Either: Potassium Citrate and/or Potassium Chloride; 150 mg (57 mg or 79 mg potassium, respectively)

Phytoceramides; 30 mg; **

Sodium Hyaluronate; 30 mg; **

**Daily Value (% RDV) not established.

In some embodiments, the quantity of the above ingredients in either dietary supplement may, per serving, be each modified by +/−100%/without departing from the teachings of this specification. In embodiments, an ingredient may be provided from a different source without departing from the teachings of this specification. In some embodiments, the range of ceramides in the dietary supplement composition is 20-90 mg, the range of hyaluronic acid is 20-90 mg, and the range of each electrolyte is +/−50%.

In some embodiments, additional optional ingredients may include: coconut water powder, pink Himalayan salt, citric acid, yuzu raspberry and other natural flavors, silica, beet juice powder, and monk fruit extract.

In embodiments of a method for using an embodiment of the dietary supplement to improve skin appearance, 1-2 sachets may be consumed daily or as directed by a healthcare professional. To consume, one sachet may be mixed with 12-16 oz of cold water, with the supplement added first, followed by the water.

Thus, in following the method using the composition listed and other embodiments, the user will receive the benefits of total cellular and skin hydration, by way of: cellular hydration and recharging via the most bioavailable chelated electrolytes (magnesium glycinate, calcium malate, potassium citrate and potassium chloride) plus full spectrum minerals (potassium from coconut water, sodium from Himalayan pink salt); powerful skin hydrating active ingredients: ceramides (from phytoceramides) and hyaluronic acid (from sodium hyaluronate); and silica, which promotes collagen production Users may receive further benefits of embodiments through one or more of the following: 1) the chelated electrolyte and full spectrum mineral stack, which provides the absolute best in bioavailability and promotes hydration on a deep cellular level while providing a cutting-edge transport system for the rapid and maximized absorption of ceramides and hyaluronic acid; 2) the combined usage of the embodiment with a skincare routine, which will help unlock synergies for internal and external moisturization, maximizing its combined potential, and multiply the benefits derived from just the skincare routine, allowing the user to extract the greatest efficacy and function from existing creams and serums, while structurally and sustainably improving the skin's natural moisture production and preservation function; 3) ceramides, which are clinically proven to increase skin hydration and elasticity while visibly reducing fine lines and dullness, thereby restoring skin barrier function and strengthening cellular integrity to reduce moisture loss; 4) hyaluronic acid, which helps the skin soak up water for a youthful, dewy glow, and the regular replenishment of which increases moisture retention; and 5) combining the chelated electrolyte and full spectrum mineral stack with trace minerals from Himalayan pink salt and pure coconut water, which is further designed to enhance rapid absorption of electrolytes and bioactive compounds into the skin.

Embodiments may include non-GMO, vegan, gluten free, and/or sugar-free compositions.

Thus, a method for improving skin appearance in which a first step includes ingesting a dietary supplement comprising at least one ceramide and at least one of: hyaluronic acid or a salt of hyaluronic acid, as further specified by any of the embodiments; and a second step includes repeating the first step daily.

The previous description is provided to enable any person skilled in the art to practice the various aspects described herein. In the embodiments, the separation of various system components in the embodiments described above should not be understood as requiring such separation in all embodiments. Various modifications to these aspects will be readily apparent to those skilled in the art, and the generic principles defined herein may be applied to other aspects. Thus, the claims are not intended to be limited to the aspects shown herein, but are to be accorded the full scope consistent with the language claims, wherein reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the subject disclosure.

A phrase such as an "aspect" does not imply that such aspect is essential to the subject technology or that such aspect applies to all configurations of the subject technology. A disclosure relating to an aspect may apply to all configurations, or one or more configurations. A phrase such as an aspect may refer to one or more aspects and vice versa. A phrase such as a "configuration" does not imply that such configuration is essential to the subject technology or that such configuration applies to all configurations of the subject technology. A disclosure relating to a configuration may apply to all configurations, or one or more configurations. A phrase such as a configuration may refer to one or more configurations and vice versa.

At times, for convenience movement and orientations may be referred to as "horizontal" or "vertical," or "up" or "down." One of skill will realize that this is with regard to the apparatus as it is illustrated in the drawing and not with reference to the Earth. All structural and functional equivalents to the elements of the various aspects described throughout this disclosure that are known or later come to be known to those of ordinary skill in the art are expressly incorporated herein by reference and are intended to be encompassed by the claims.

What is claimed is:

1. A dietary supplement comprising: at least one ceramide, greater than 0 mg and up to and including 120 mg of sodium hyaluronate, calcium, magnesium, sodium, and potassium.

2. The dietary supplement of claim 1, wherein:
- the calcium is included as calcium malate;
- the magnesium is included as magnesium glycinate;
- the sodium is included as at least one of: sodium citrate or sodium chloride; and
- the potassium is included as at least one of: potassium citrate or potassium chloride.

3. The dietary supplement of claim 1, wherein a daily serving includes:
- from greater than 0 mg up to and including 120 mg of calcium;
- from greater than 0 mg up to and including 400 mg of magnesium;
- from greater than 0 mg up to and including 600 mg of sodium, not including sodium from sodium hyaluronate;
- from greater than 0 mg up to and including 600 mg of potassium;
- from greater than 0 mg up to and including 120 mg of at least one phytoceramide; and
- from greater than 0 mg up to and including 120 mg of sodium hyaluronate.

4. The dietary supplement of claim 1, wherein a daily serving includes:
- from greater than 0 mg up to and including 60 mg of calcium;
- from greater than 0 mg up to and including 200 mg of magnesium;
- from greater than 0 mg up to and including 300 mg of sodium, not including sodium from sodium hyaluronate;
- from greater than 0 mg up to and including 300 mg of potassium;
- from greater than 0 mg up to and including 60 mg of at least one phytoceramide; and
- from greater than 0 mg up to and including 60 mg of sodium hyaluronate.

5. The dietary supplement of claim 1, wherein a daily serving includes:
- from 15 mg to 45 mg of calcium;
- from 50 mg to 150 mg of magnesium;
- from 75 mg to 225 mg of sodium, not including sodium from sodium hyaluronate;
- from 75 mg to 225 mg of potassium;
- from 20 mg to 90 mg of at least one phytoceramide; and
- from 20 mg to 90 mg of sodium hyaluronate.

6. The dietary supplement of claim 1, wherein a daily serving includes:

from 4 mg to 10 mg of calcium;
from 7 mg to 21 mg of magnesium;
from 20 mg to 88 mg of sodium, not including sodium from sodium hyaluronate;
from 29 mg to 118 mg of potassium;
from 20 mg to 90 mg of at least one phytoceramide; and
from 20 mg to 90 mg of sodium hyaluronate.

7. The dietary supplement of claim 1, further comprising one or more ingredients chosen from a list consisting of: coconut water powder, pink Himalayan salt, citric acid, yuzu raspberry natural flavor, silica, beet juice powder, and monk fruit extract.

8. A method of improving skin appearance comprising:
ingesting a dietary supplement comprising: at least one ceramide, greater than 0 mg and up to and including 90 mg of sodium hyaluronate,
calcium, magnesium, sodium, and potassium.

9. The method of claim 8, wherein:
the calcium is included as calcium malate;
the magnesium is included as magnesium glycinate;
the sodium is included as at least one of: sodium citrate or sodium chloride; and
the potassium is included as at least one of: potassium citrate or potassium chloride.

10. The method of claim 8, wherein the daily serving includes:
from greater than 0 mg up to and including 120 mg of calcium;
from greater than 0 mg up to and including 400 mg of magnesium;
from greater than 0 mg up to and including 600 mg of sodium, not including sodium from sodium hyaluronate;
from greater than 0 mg up to and including 600 mg of potassium;
from greater than 0 mg up to and including 120 mg of at least one phytoceramide; and
from greater than 0 mg up to and including 120 mg of sodium hyaluronate.

11. The method of claim 8, wherein the daily serving includes:
from greater than 0 mg up to and including 60 mg of calcium;
from greater than 0 mg up to and including 200 mg of magnesium;
from greater than 0 mg up to and including 300 mg of sodium, not including sodium from sodium hyaluronate;
from greater than 0 mg up to and including 300 mg of potassium;
from greater than 0 mg up to and including 60 mg of at least one phytoceramide; and
from greater than 0 mg up to and including 60 mg of sodium hyaluronate.

12. The method of claim 8, wherein the daily serving includes:
from 15 mg to 45 mg of calcium;
from 50 mg to 150 mg of magnesium;
from 75 mg to 225 mg of sodium, not including sodium from sodium hyaluronate;
from 75 mg to 225 mg of potassium;
from 20 mg to 90 mg of at least one phytoceramide; and
from 20 mg to 90 mg of sodium hyaluronate.

* * * * *